US011452812B2

(12) United States Patent
Halamish et al.

(10) Patent No.: US 11,452,812 B2
(45) Date of Patent: Sep. 27, 2022

(54) INJECTION APPARATUS AND METHOD FOR USE

(71) Applicant: Target Point Technologies Ltd, Yokneam Illit (IL)

(72) Inventors: Asaf Halamish, Pardes Hanna-Karkur (IL); Gershon Goldenberg, Pardes Hanna-Karkur (IL)

(73) Assignee: pHi-Tech Animal Health Technologies Ltd., Airport City (IL)

( * ) Notice: Subject to any disclaimer, the term of this patent is extended or adjusted under 35 U.S.C. 154(b) by 138 days.

(21) Appl. No.: 16/667,405

(22) Filed: Oct. 29, 2019

(65) Prior Publication Data
US 2020/0061284 A1 Feb. 27, 2020

Related U.S. Application Data

(63) Continuation of application No. PCT/IB2018/052958, filed on Apr. 28, 2018.
(Continued)

(51) Int. Cl.
*A61M 5/14* (2006.01)
*A61M 5/158* (2006.01)
(Continued)

(52) U.S. Cl.
CPC ............. *A61M 5/1407* (2013.01); *A61D 7/00* (2013.01); *A61M 5/1413* (2013.01);
(Continued)

(58) Field of Classification Search
CPC ............ A61D 1/02; A61D 1/025; A61D 7/00; A61M 2005/14268; A61M 2005/14272;
(Continued)

(56) References Cited

U.S. PATENT DOCUMENTS

| 4,276,879 A | 7/1981 | Yiournas |
| 4,673,395 A * | 6/1987 | Phillips ............. A61M 5/31581 604/191 |

(Continued)

FOREIGN PATENT DOCUMENTS

| CA | 2959162 | 3/2016 |
| CN | 1791440 A | 6/2006 |

(Continued)

OTHER PUBLICATIONS

Office action for European Application No. EPC 14876301.4 dated Mar. 10, 2020 (3 pages).

(Continued)

*Primary Examiner* — Quynh-Nhu H. Vu
(74) *Attorney, Agent, or Firm* — Klarquist Sparkman, LLP

(57) ABSTRACT

An injection apparatus for sequentially injecting a patient with at least two medicaments may include a hand-held unit comprising a grip for being held by an operator, a single needle, a base unit coupled to the hand-held unit via at least one connecting tube, at least two containers for holding medicaments removably coupled to the base unit, and at least one pump. The at least one connecting tube can be flexible enough to enable easy maneuvering of the hand-held unit and rigid enough to prevent widening of the tube due to inner pressure when medicaments pass from the containers to the hand-held unit. The injection apparatus can be used to administer the at least two medicaments sequentially at different injection points.

18 Claims, 13 Drawing Sheets

Related U.S. Application Data

(60) Provisional application No. 62/492,492, filed on May 1, 2017.

(51) Int. Cl.
*A61M 39/10* (2006.01)
*A61M 5/20* (2006.01)
*A61M 5/142* (2006.01)
*A61D 7/00* (2006.01)

(52) U.S. Cl.
CPC ........ *A61M 5/14244* (2013.01); *A61M 5/158* (2013.01); *A61M 5/20* (2013.01); *A61M 39/10* (2013.01)

(58) Field of Classification Search
CPC .. A61M 2005/1787; A61M 2005/2013; A61M 2005/3128; A61M 2205/106; A61M 2205/3673; A61M 39/10; A61M 39/24; A61M 5/1407; A61M 5/1408; A61M 5/1413; A61M 5/14216; A61M 5/14244; A61M 5/158; A61M 5/19; A61M 5/20; A61M 5/204; A61M 5/2066; A61M 5/31568; A61M 5/3202; A61M 5/3293; A61M 5/3294; A61M 5/445; A61M 5/46
See application file for complete search history.

(56) References Cited

U.S. PATENT DOCUMENTS

| | | | |
|---|---|---|---|
| 4,717,383 A | | 1/1988 | Phillips et al. |
| 4,985,015 A | * | 1/1991 | Obermann ........ A61M 5/14216 604/152 |
| 5,320,162 A | * | 6/1994 | Seaman .................... B01L 7/00 165/255 |
| 5,807,336 A | * | 9/1998 | Russo .................... A61M 5/172 604/131 |
| 6,858,020 B2 | | 2/2005 | Rusnak |
| 7,056,307 B2 | | 6/2006 | Smith et al. |
| 7,217,254 B2 | * | 5/2007 | Kirwan ............ A61B 17/00491 604/82 |
| 8,029,469 B2 | | 10/2011 | Ethelfield |
| 8,529,522 B2 | | 9/2013 | Cohen |
| 9,706,754 B2 | * | 7/2017 | Prescott .................. A61M 5/19 |
| 10,258,445 B2 | * | 4/2019 | Halamish ............... A61D 1/025 |
| 10,624,567 B2 | * | 4/2020 | Feldman ............ A61B 5/14532 |
| 2001/0008961 A1 | | 7/2001 | Hecker |
| 2002/0183616 A1 | | 12/2002 | Toews |
| 2005/0043681 A1 | | 2/2005 | Rusnak |
| 2005/0209569 A1 | | 9/2005 | Ishikawa et al. |
| 2006/0135910 A1 | | 6/2006 | Luther et al. |
| 2008/0060970 A1 | * | 3/2008 | Wheeler ............ A61B 17/0057 604/82 |
| 2008/0114305 A1 | | 5/2008 | Gerondale |
| 2008/0177223 A1 | | 8/2008 | Johnston et al. |
| 2009/0018505 A1 | | 1/2009 | Arguedas et al. |
| 2009/0163860 A1 | * | 6/2009 | Patrick ..................... A61B 8/00 604/83 |
| 2009/0198215 A1 | | 8/2009 | Chong |
| 2010/0130960 A1 | | 5/2010 | Spire |
| 2011/0046454 A1 | * | 2/2011 | Ejlersen ............ A61M 37/0069 604/117 |
| 2012/0053457 A1 | * | 3/2012 | Fago .................. A61M 5/14546 600/432 |
| 2012/0073515 A1 | | 3/2012 | Chung et al. |
| 2014/0114258 A1 | | 4/2014 | Day |
| 2015/0128873 A1 | | 5/2015 | Prescott et al. |
| 2015/0174321 A1 | * | 6/2015 | Cohen ............... A61M 5/16827 604/506 |
| 2016/0038266 A1 | * | 2/2016 | Edwards ............ A61M 5/2053 604/65 |
| 2016/0101240 A1 | | 4/2016 | Samson |
| 2016/0235512 A1 | | 8/2016 | Miller et al. |
| 2016/0263321 A1 | | 9/2016 | Eisele et al. |
| 2016/0296313 A1 | | 10/2016 | Fleming et al. |
| 2016/0324613 A1 | * | 11/2016 | Halamish ................. A61D 7/00 |
| 2017/0197037 A1 | | 7/2017 | Edwards |
| 2019/0183622 A1 | * | 6/2019 | Halamish .......... A61M 5/31546 |

FOREIGN PATENT DOCUMENTS

| | | |
|---|---|---|
| CN | 102105183 | 6/2011 |
| CN | 203208448 U | 9/2013 |
| CN | 104812334 A | 7/2015 |
| CN | 105682607 A | 6/2016 |
| CN | 106029004 A | 10/2016 |
| CN | 107468372 | 12/2017 |
| EP | 2285436 | 10/2015 |
| EP | 3089703 A1 | 11/2016 |
| GB | 2233234 | 1/1991 |
| WO | WO 2004/101060 | 11/2004 |
| WO | WO 2008/057223 | 5/2008 |
| WO | WO 2008/079824 | 7/2008 |
| WO | 2009/134577 | 11/2009 |
| WO | WO 2010/052579 | 5/2010 |
| WO | WO 2012/176029 | 12/2012 |
| WO | WO 2013/064475 | 5/2013 |
| WO | WO 2014/016807 | 3/2014 |
| WO | WO 2014/107766 | 7/2014 |
| WO | WO 2015/101981 | 7/2015 |
| WO | WO 2017/086807 | 5/2017 |
| WO | WO 2017/086924 A1 | 5/2017 |
| WO | WO 2018/092138 A1 | 5/2018 |
| WO | WO 2018/203203 A1 | 11/2018 |

OTHER PUBLICATIONS

Office action for Brazil Application No. BR112016015342, dated May 13, 2020 (3 pages).
Office Action for Mexican Application No. MX/a/2016/008647, dated Nov. 7, 2019 (4 pages) (5 pages of translation).
Office Action for Israeli Application No. 246538, dated Dec. 12, 2019 (4 pages, translation incorporated into Office Action).
Office Action for Chinese Application No. 201880029105.6, dated Jun. 2, 2021 (24 pages, with English translation).
Office Action for Mexican Application No. MX/a/2016/008647, dated Jul. 19, 2019 (3 pages); (4 pages of translation included).
International Search Report & Written Opinion, PCT/IB2018/059883, dated Mar. 25, 2019 (11 pages).
International Search Report & Written Opinion, PCT/IB2018/052958, dated Aug. 12, 2018 (14 pages).
European Search Report, EP 14876301.4, dated Aug. 3, 2017 (3 pages).
Examination Report for European Application No. EP 18794760.1, issued by the European Patent Office dated Aug. 6, 2021 (8 pages).
Examination Report for Russian Patent Application No. 2019136958, issued by the Russian Patent Office dated Aug. 18, 2021 (20 pages).
International Search Report & Written Opinion, PCT/IB2020/053177, dated Jul. 19, 2020 (20 pages).
Extended European Search Report, dated Sep. 1, 2020, European Patent Application No. EPC 18794760.1, filed Apr. 28, 2018 (10 pages).
Examination Report for European Application No. EP 18888570.1, issued by the European Patent Office dated Oct. 25, 2021 (13 pages).
Office action for Chinese Application No. 201880079657.8 (includes translation), dated Oct. 27, 2021 (13 pages).
Office Action for Chinese Application No. 201880029105.6 dated Dec. 28, 2021 (with translation) (20 pages).
Office Action for Indian Application No. 201917048613 dated Feb. 17, 2022 (with translation) (5 pages).

* cited by examiner

INJECTION APPARATUS AND METHOD FOR USE

CROSS REFERENCE TO RELATED APPLICATION

This application is a continuation of PCT/IB2018/052958, entitled "INJECTION APPARATUS AND METHOD FOR USE," filed on Apr. 28, 2018, which application claims the benefit of the earlier filing date of U.S. Provisional Application No. 62/492,492, entitled "REMOTE DOUBLE-INJECTION APPARATUS," filed on May 1, 2017. Both of these prior applications are incorporated herein by reference in their entirety.

FIELD

The present disclosure concerns injector devices for injecting patients, particularly livestock animals, and more particularly concerns the field of automatic injectors, with certain embodiments concerning injecting a large number of animals (e.g. swine, poultry, or aquatic species including fish) sequentially and/or with more than one compound and/or medicament.

BACKGROUND

In the livestock industry, animals often must be administered substances such as medications, for a variety of reasons. Typically, each producer must treat large numbers of animals. Treatment can often require injecting each animal with a plurality of medications, generally in liquid form. Such medications can include medicines, vaccines, hormones, food supplements and the like (hereinafter referred to generally as "medicament").

Administering such medicaments typically includes using an administration device, such as a syringe or drenching unit, from which a medicament dose is either manually or automatically administered to the animal. This type of administration typically includes hand actuation or pumping of the medication device to deliver the medication to the animal.

When treating a large number of animals (e.g., via a hand actuated device), the operator may become fatigued. This can result in a number of malfunctions, for example: (i) accidental self-injection by the operator; (ii) administering the medicament dose when the needle has not yet penetrated the patient's skin or has not yet penetrated to the desired depth; (iii) administering the dose after the needle has been removed from the patient; (iv) administering only a portion of the required dose; (v) inserting the needle into the patient in a non-optimal orientation; and/or (vi) administering a duplicate dose to the same individual, among others.

Additionally, in many cases it is necessary to administer more than one medicament to a single animal. In cases where there is no ready composition of the different medicaments, or where it is not possible to combine two or more medicaments together, more than one injection must be performed per patient, contributing to operator fatigue. For this purpose, several devices have been developed for administering two or more separate medicaments to a single patient in a single penetration and administration step. These devices usually comprise several needles, one for each medicament to be administered, thus allowing each medicament to be administered simultaneously at a different injection point. However, such devices have several drawbacks, such as a permanent distance between the different needles, which presents certain physical limitations, especially when injecting small size animals. This can prevent the same device from being used on animals of varying species or sizes, and can increase production costs by requiring a user to purchase multiple devices. Other devices comprise a "pre-mixing" step for first mixing the different medicaments and then administering the mixture through a single needle at a single injection point. However, such devices are suitable only for medicaments that can be pre-mixed and administered at the same injection location.

Furthermore, since there are generally a large number of animals and the process is typically done very quickly, it is sometimes difficult or impossible to monitor which individuals were actually injected. Moreover, with some prior devices it is not possible to monitor the individuals that have received a full dose of medicament versus those who did not receive a full dose. These kinds of malfunctions cause additional costs and complications to the livestock rearing process, such as illness outbreaks due to improperly-treated animals.

Some prior devices have been developed that attempt to address some of these possible malfunctions. For example, U.S. Publication No. 2009/0018505 discloses a powered automatic injection device having a hand-held gun-shaped with a handgrip. The device has an internal motor powered by connection to a power source, such as AC current or DC battery. A pair of limit-switches controls the delivery of the medicament by limiting the movement of a helical gear that moves a fitting in response to being powered by the internal motor.

GB 2233234 discloses a portable jet injector for avian vaccination that may include two ejection chambers fed separately with different vaccine compositions for being administrated simultaneously to one bird.

WO 2004/101060 discloses an injector assembly adapted to be carried by an operating person. A contact sensor and positioning sensor delivers information to a controller, which in turn controls a propelling unit, a dosing unit, and the needle to automatically push the medical material. The injector assembly may comprise an electronic or physical marker for recording.

U.S. Pat. No. 6,858,020 discloses an automatic repeater vaccinator apparatus for dispensing a predetermined volume of a fluid into an animal, and reloading after each volume of fluid is dispensed.

U.S. Pat. No. 8,529,522 discloses an injection apparatus having a removable needle cartridge, wherein the cartridge comprises a plurality of needles. Each of the needles is advanced into a deployment position by an advancer.

WO 2014/016807 discloses a mass vaccination device that can electronically control and deliver a measured amount of a vaccine through a needle.

U.S. Publication No. 2008/0177223 discloses an injection system that may deliver at least two fluid doses to a small bird by penetrating the skin of the recipient bird with at least one injection needle.

U.S. Publication No. 2005/0209569 discloses an injection device, in which only after the device is pressed against the body of a patient, a needle automatically protrudes from the device into the patient for administering the medicament, and is then immediately removed, thereby reducing pain.

However, known devices suffer from various disadvantages. For example, many are stationary, manually actuated, require cumbersome injection operation, require multiple needles, or suffer from a lack of sterilization, among other issues.

Accordingly, there is a continuing need for improved injector devices and methods for their use, such as devices for injecting a large number of animals sequentially, often with multiple medicaments.

SUMMARY

In accordance with the present disclosure, described herein are embodiments of an injection apparatus for injecting two or more different medicaments into a patient in two or more different locations using a single needle. The injection apparatuses can be used to inject a large number of animals (e.g. swine, poultry, fish, sheep, goats, cattle, etc.) with medicament in a quick and efficient manner in order to prevent and/or reduce operator error, operator fatigue, and injection malfunction.

Accordingly, in some embodiments, an injection apparatus for sequentially injecting a patient with at least two medicaments includes a hand-held unit comprising a grip for being held by an operator, a single needle, a base unit coupled to the hand-held unit via at least one connecting tube, at least two containers for holding medicaments removably coupled to the base unit, and at least one pump. The at least one connecting tube can be flexible enough to enable easy maneuvering of the hand-held unit and rigid enough to prevent widening of the tube due to inner pressure when medicaments pass from the containers to the hand-held unit. The injection apparatus can be used to administer the at least two medicaments sequentially at different injection points.

In a representative embodiment, an injection apparatus comprises a single needle and a plurality of dosing chambers fluidly coupled to the single needle. In some embodiments, the injection apparatus can further comprise a plurality of medicament containers, each medicament container being fluidly coupled to a dosing chamber of the plurality of dosing chambers. In some embodiments, one or more flexible tubes can be used to couple the dosing chambers and the plurality of medicament containers, and the flexible tubes can be configured to resist widening when medicament passes through them.

In another representative embodiment, an injection apparatus comprises a hand-held unit comprising a gripping portion, a head portion, and a single needle; a plurality of dosing chambers fluidly coupled to the single needle; a base unit coupled to a plurality of medicament containers; at least one flexible connecting tube fluidly coupling the hand-held unit and the base unit, the flexible tube configured to resist widening when medicament passes through it. In some embodiments, the injection apparatus can comprise one or more pumps configured to pump medicament from the base unit to the hand-held unit.

In some embodiments, the head portion can be stationary relative to the hand-held unit and the single needle can be coupled to and extend from the stationary head portion. In other embodiments, the head portion can be movable relative to the hand-held unit, and urging the movable head portion against the body of a patient can expose the single needle.

In some embodiments, the base unit of the injection apparatus is configured to be worn by a user. In some embodiments, the injection apparatus further comprises a temperature control unit, for example, a Peltier heating and cooling system. In some embodiments, the injection apparatus further comprises a control panel configured to determine and display information relating to an injection process. In some embodiments, the control panel is configured to transmit data in real-time to a remote device. In some embodiments, the injection apparatus further comprises a plurality of valves, each valve being coupled to a medicament container. In some embodiments, the injection apparatus can further comprise a malfunction-identification system. In some embodiments, the injection apparatus can have a plurality of pumps, and each pump can be coupled to one of the plurality of medicament containers.

In some embodiments, the injection apparatus is configured to administer a plurality of medicaments sequentially at a plurality of injection sites. In some embodiments, the medicament is administered via manual actuation of the injection apparatus. In other embodiments, the medicament can be administered automatically upon insertion of the single needle to a selected depth within a patient.

In another representative embodiment, an injection apparatus can comprise: a hand-held unit comprising a gripping portion, a head portion, and a single needle; a plurality of dosing chambers fluidly coupled to the single needle; a base unit coupled to a plurality of medicament containers; at least one flexible connecting tube fluidly coupling the hand-held unit and the base unit, the flexible connecting tube configured to resist widening upon passage of the medicament therethrough; at least one pump configured to pump medicament from the base unit to the hand-held unit; one or more temperature control units operatively coupled to the medicament containers; one or more control panels configured to determine and display information relating to an injection process and to optionally transmit real-time data to a remote device; and a malfunction-identification device configured to identify malfunction of the injection apparatus.

The foregoing and other objects, features, and advantages of the disclosure will become more apparent from the following detailed description, which proceeds with reference to the accompanying figures.

DETAILED DESCRIPTION

I. Definitions

Figure 1:
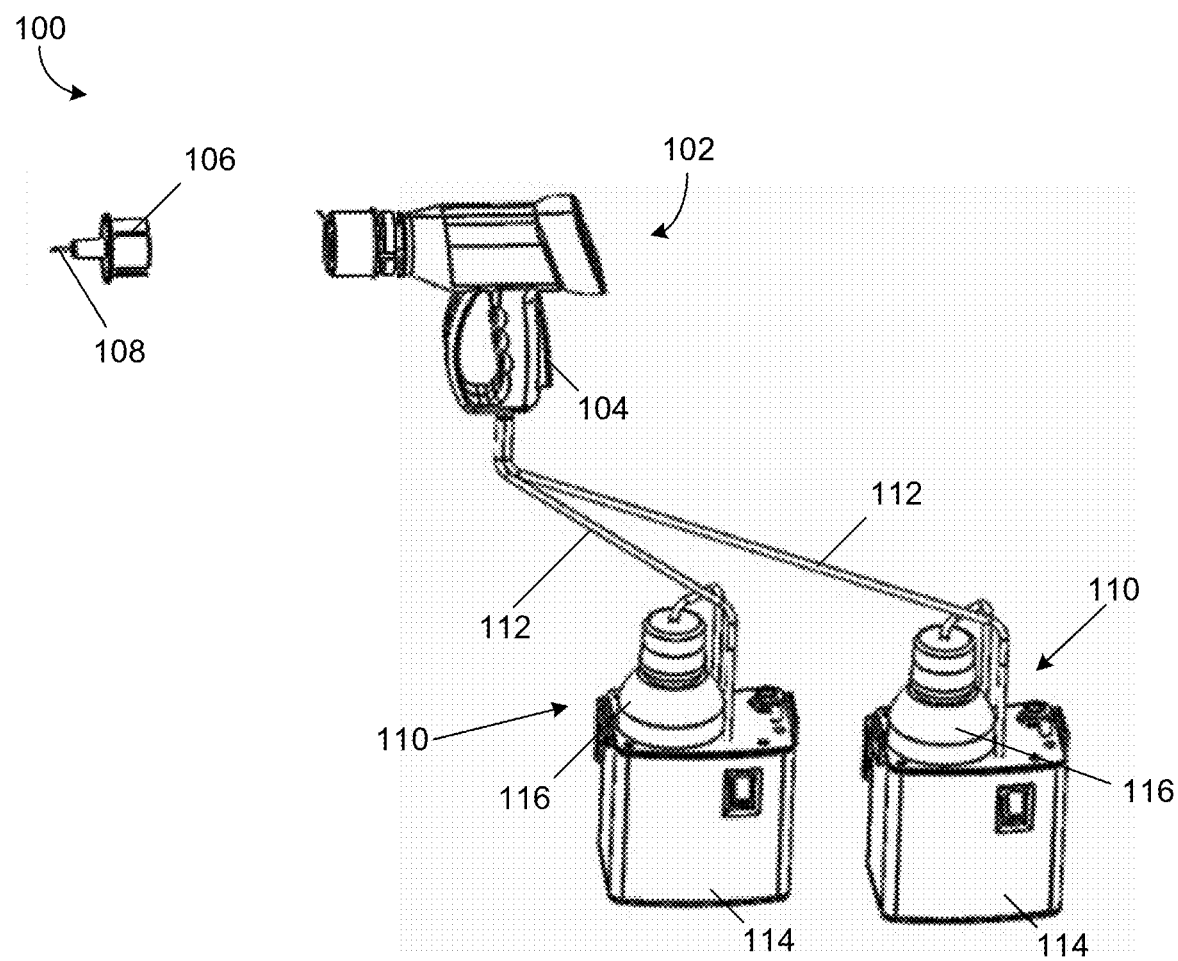
FIG. 1 is a side view of an exemplary injection apparatus.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the injection site. As used herein, the term "distal" refers to a position, direction, or portion of a device that is further away from the user and closer to the injection site. Thus, for example, proximal motion of a device is motion of the device away from the injection site and toward the user (e.g., away from the patient's body), while distal motion of the device is motion of the device away from the user and toward the injection site (e.g., into the patient's body). The terms "longitudinal" and "axial" refer to an axis extending in the proximal and distal directions, unless otherwise expressly defined.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

As used herein, the term "approximately" means the listed value and any value that is within 10% of the listed value. For example, "approximately 100 degrees" means any value between 90-110 degrees, inclusive.

The term "medicament" as used herein refers to any material that needs to be injected to a patient, and includes, e.g., antibiotics, vaccines, hormones, food supplements, oils, vitamins, minerals, etc. In some embodiments, the medicaments are in liquid form. In other embodiments, the medicaments may be in powdered form and may be mixed with one or more solvents within the two or more containers or prior to being disposed therein.

II. Exemplary Embodiments

Disclosed herein are embodiments of injection apparatuses used to administer two or more medicaments to a patient at discrete injection sites using a single needle, and methods for using the same.

A representative injection apparatus 100 is shown in FIG. 1. In certain embodiments, injection apparatus 100 is useful for injecting at least two medicaments sequentially into a patient. Certain disclosed embodiments can comprise a hand-held unit 102 having a grip 104 for being held by an operator, a separable head portion 106, and a single needle 108 extending from and/or contained within the head portion. The apparatus can further comprise a base unit 110, coupled to the hand-held unit 102 via at least one connecting tube 112 and an electric wire (not shown) for powering the hand-held unit 102 from the base unit 110 and for communicating information from one unit to another.

The base unit 110 can comprise a plurality of containers 114 (e.g., two in the illustrated embodiment) for containing medicaments. The containers 114 can be removably coupled to the base unit 110 or they can be remote from the base unit and connected thereto by tubing. For example, in the illustrated embodiment, the injection apparatus includes a first container and a second container removably coupled to the base unit 110. In the illustrated embodiment, the first and second containers have the same size and shape, however in other embodiments the containers 114 may be of different sizes, shapes, opacities, etc.

The containers can be connected to the hand-held unit 102 via one or more connecting tubes 112 (e.g., two in the illustrated embodiment) and at least one pump 116. For at least certain embodiments, the at least one connecting tube 112 is sufficiently flexible to allow a user to maneuver the hand-held unit and rigid enough to prevent widening of the connecting tube 112 due to inner pressure when passing medicaments from the containers 114 to the hand-held unit 102. Widening of the tube can cause inaccurate dosing of medicament. The injection apparatus can be configured to administer two or more medicaments sequentially at different injection points.

In some embodiments, the base unit 110 is configured to be worn, carried, or otherwise easily transported by a user (e.g., on a belt, in waist bag, a vest, or in a carryon bag). The connecting tube 112 can be flexible enough to enable the user to move the hand-held unit 102 in any direction and can be long enough to enable said user to fully extend his or her arm while holding the hand-held unit 102. The connecting tube 112 can also be rigid enough (e.g., non-expandable and non-deformable) to prevent widening of the tube due to the pressure of the passing medicaments. Widening of the connecting tube can lead to inaccurate dosing of the medicament or to a delay between pump action and the administration of the medicament to the patient. In some embodiments, the connecting tube can flex in all directions and can withstand twisting. In some embodiments, the connecting tube can elastically return to its original shape after being bent, twisted, extended, or otherwise deformed. For example, the tube can have an outer diameter of generally from about 1 mm to 10 mm, and more typically from about 4 mm to 5 mm in size. The internal diameter can be generally from about 1 mm to 5 mm, and more typically from about 2 mm to 3 mm. In some embodiments, the tube can be formed from polyamide. In some embodiments, the tube can further comprise a spring that allows the tube to have flexibility in all directions while resisting expansion of the tube. The spring can be external to the tube, internal to the tube, and/or formed integrally with the tube.

In some embodiments, the rigidity of the connecting tube 112 is achieved by using a casing in conjunction with an elastic tube. In some embodiments, the casing can be formed separately and either wrapped around the elastic tube or placed inside the tube. In other embodiments, the casing can be formed integrally with the tube. In still other embodiments, the elastic tube can be formed of a material having a rigidity capable of withstanding the forces applied by the internal passage of fluids.

In some embodiments, the connecting tube 112 can be fabricated by laser cutting stainless steel to create integral links having a design that allows the tube to be flexible, while preventing radial expansion of the tube. Once laser cut, the resulting laser-cut steel tube is either mounted onto a flexible tube made of polymeric or elastomeric material, or coated with such a material.

In some embodiments, each medicament of the two or more medicaments can be administered by manual actuation of the injection apparatus, for example, by manually pressing and/or pulling a trigger. The trigger can be a lever or button located on the hand-held unit. In such embodiments, each press of the trigger will administer a predetermined amount of each of the medicaments to be administered. For example, in an embodiment for administering two medicaments, a first press of the trigger will administer a selected dose of a first medicament, and a second press of the trigger will administer a selected dose of a second medicament.

In other embodiments, each medicament can be administered automatically when the needle reaches a selected location (e.g., depth) within the patient. For example, in such embodiments, the injection apparatus can further comprise a needle sensor for first determining that the needle has been sufficiently inserted into the patient's body, and a control apparatus for activating at least one pump 116 configured to deliver a predetermined amount of each medicament after the needle is inserted appropriately into a patient. The needle penetration depth can vary for different patient species, sizes, and/or ages. For certain applications, the needle is inserted to a depth of greater than 0 mm to 20 mm, and more typically from about 1 mm to 15 mm.

Figure 2:
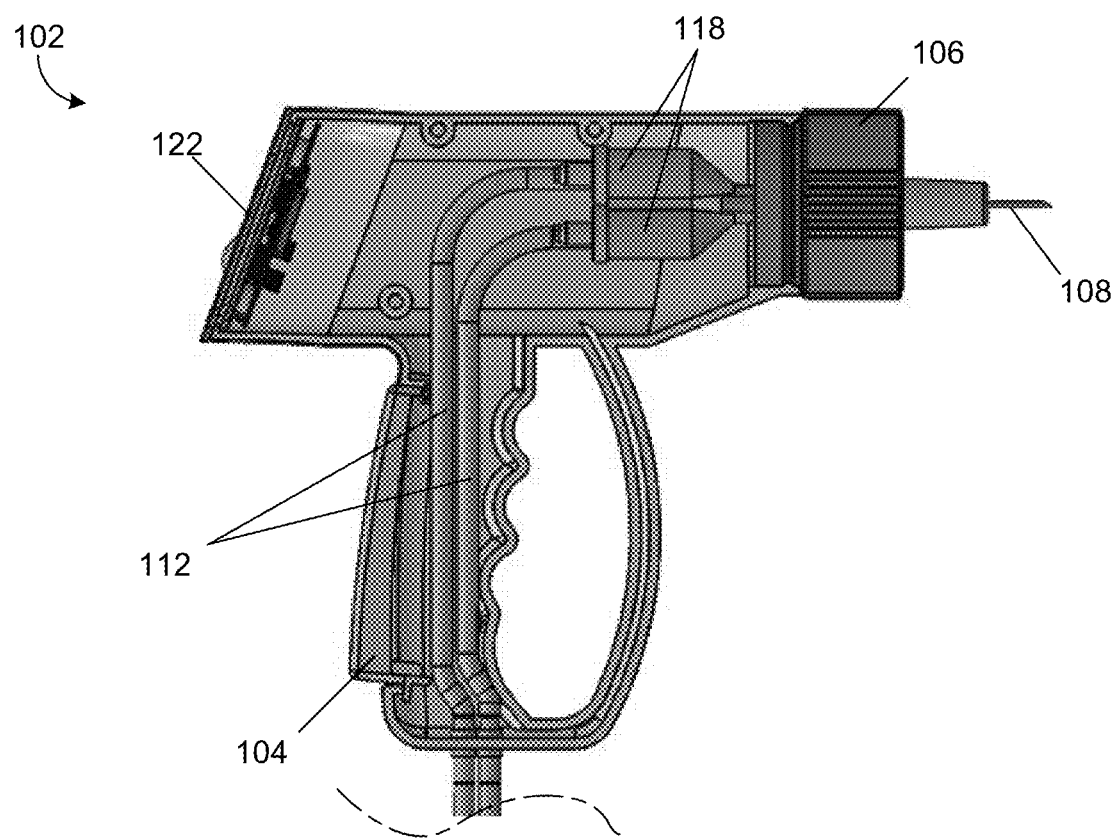
FIG. 2 is a partial cross-sectional view of an exemplary hand-held unit.

In some embodiments, as shown in FIGS. 1 and 2, the single needle 108 of the injection apparatus can be a straight needle extending distally from the head portion 106 of the hand-held unit 102. In other embodiments, the needle can be curved such that it can extend laterally under the skin of a patient when inserted thereinto. In the illustrated embodiment, the needle is stationary with respect to the head portion. However, in other embodiments, the needle can be movable and/or retractable with respect to the head portion 106. In such embodiments, the needle can be axially movable with respect to the hand-held unit 102 and/or the head portion 106 holding said needle. In some embodiments, a medicament dose can be administered automatically when the needle has reached a predetermined extended position relative to the hand-held unit and/or a predetermined depth within the patient's body.

In some embodiments, the needle of the injection apparatus can be stationary and the hand-held unit 102 can further comprise a movable head portion. In such embodiments, urging the movable head portion proximally with respect to a body portion of the hand-held unit exposes a distal edge of the stationary needle and allows it to be inserted into the patient's body. In some embodiments, the movable head and the needle may comprise a single unit that can be removed and assembled onto said hand-held unit. Further details of the movable head assembly can be found, for example, in U.S. Patent Application Publication No. 2016/0324613 which is incorporated by reference herein in its entirety.

Figure 3:
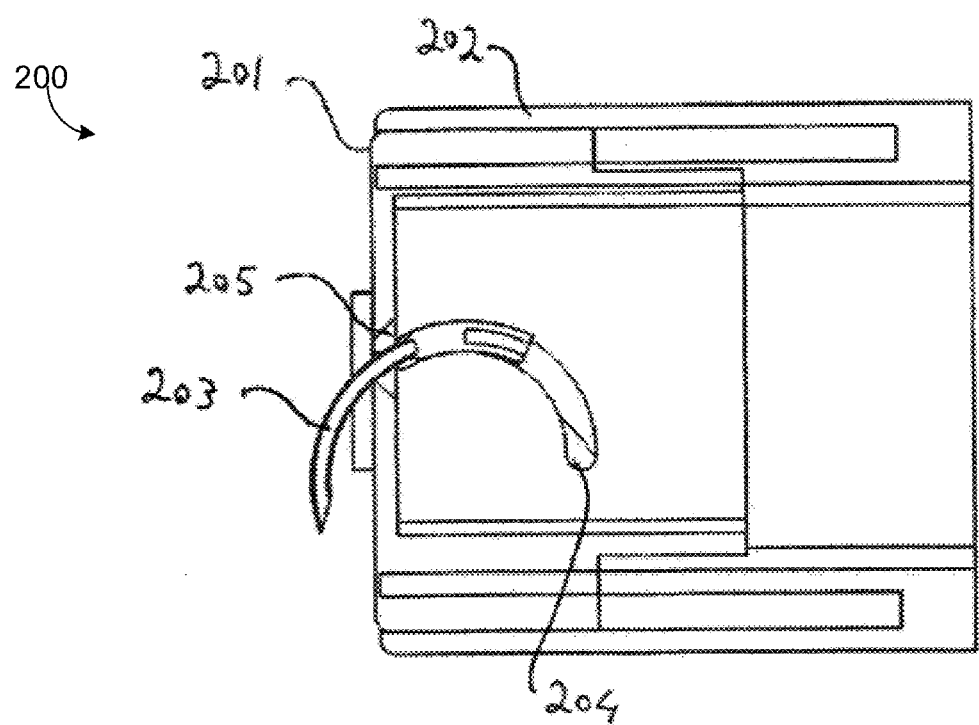
FIG. 3 is an exemplary head portion of a hand-held unit having a curved needle.

As shown in FIG. 3, in a particular embodiment 200 wherein the needle is a curved needle 203, the head portion 201 can be a movable head portion comprising a curved notch 204 in which the curved needle is disposed. When the movable head portion 201 moves proximally with respect to the hand-held unit 202 of the injection apparatus, the curved needle 203 advances distally with respect to the movable head through an opening 205 in the movable head 201 such that the curved needle 203 can pierce the patient subcutaneously without penetrating deeply into the patient's muscle or tissue. Further details of the curved needle injection method can be found, for example, in U.S. Patent Application Publication 2016/0324613.

At times it may be necessary to administer medicaments to patients (e.g., animals) of differing sizes and/or species, which can require using needles of differing type and/or size. Accordingly, in some embodiments, the injection apparatus is configured to enable easy needle replacement, either for maintenance, replacement, or adjusting the needle type and size. In some embodiments, the hand-held unit 102 of the injection apparatus 100 can comprise a replaceable and/or removable needle head (see FIG. 1). This enables a user to switch between needle types (e.g., between needles having differing lengths and/or widths, between subdermal or subcutaneous needles, between stationary and movable needles, etc.) and/or replace damaged needles.

Referring again to FIG. 2, in some embodiments, the injection apparatus further comprises one or more dosing chambers for holding a medicament dose and one or more plungers or pistons for pushing and/or pulling the medicament out of the dosing chambers. In the illustrated embodiment, the one or more dosing chambers 118 are located in the hand-held unit 102. In such embodiments, the hand-held unit 102 can comprise a dosing chamber 118 for each medicament to be injected, or can comprise a single dosing chamber. A single dosing chamber 118 can receive a different medicament before each injection according to the order of injections. For example, a second medicament can be loaded automatically into the single dosing chamber after administration of a first medicament to the patient. In still other embodiments, disclosed devices can include a plurality of dosing chambers 118 (e.g., one for each container) each coupled to a different container, and each dosing chamber can be filled with a single type of medicament, which is then delivered to the needle according to the order of injections.

The injection apparatus can comprise a plunger or piston disposed within the dosing chamber, which can be actuated (e.g., automatically or by manual actuation), to push the medicament through the needle and into the patient, as discussed in more detail below.

Figure 4:
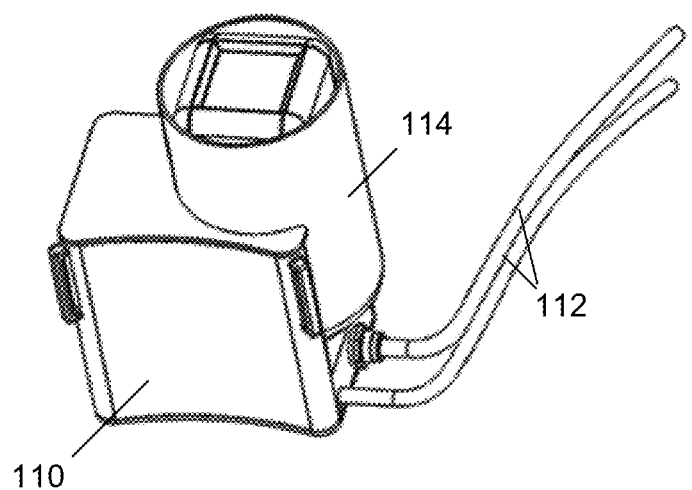
FIG. 4 is a perspective view of an exemplary of a base unit.
Figure 5:
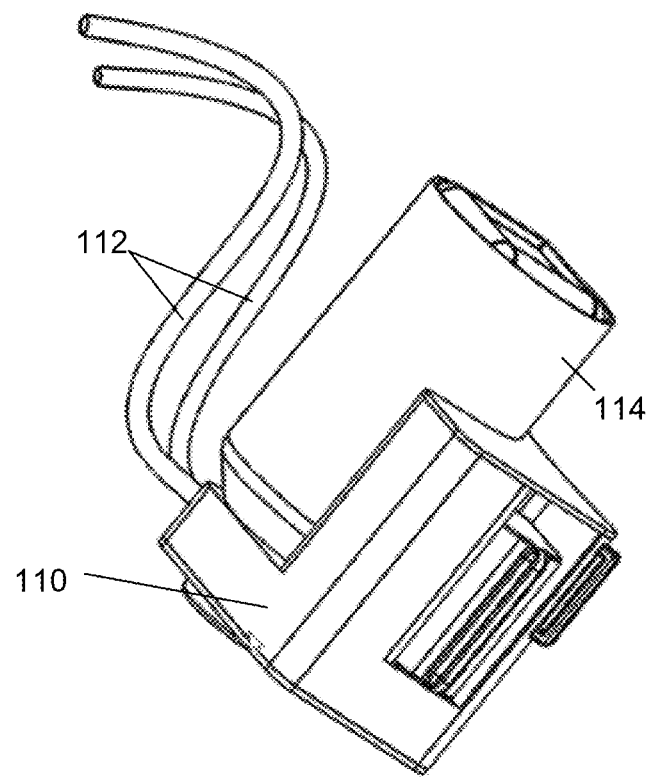
FIG. 5 is a perspective view of the base unit of FIG. 4.

Referring now to FIGS. 4-5, in some embodiments, the containers 114 can be formed separately and can be removably couplable to the base unit 110. In such embodiments, the containers can either be refilled or replaced with full containers when emptied. In other embodiments, the two or more containers 114 can be formed integrally as part of the base unit 110 and can be refilled with a suitable liquid medicament when emptied. In some embodiments, the containers 114 can be made of rigid material (e.g., a metal or a rigid polymeric material). In other embodiments, the containers 114 can be made of flexible material (e.g. a plastic bag or a flexible polymeric material). In some embodiments, the containers 114 can be transparent or substantially transparent, thus allowing a user to see the content and the level of content within. In other embodiments, the containers 114 can be opaque, for example, when the medicament(s) they hold are light-sensitive.

As discussed above, the medicaments are generally administered in a liquid form. In some embodiments, the containers 114 are provided with a ready-for-use liquid medicament. However, in other embodiments, the medicaments can be provided in a dried and/or powdered form, and can be dissolved in liquid prior to use. In still other embodiments, the containers 114 are provided with a medicament that needs to be processed or prepared prior to use (e.g. by the addition of water or other solvent thereto). Accordingly, in some embodiments, the containers 114 can be internally divided into two or more compartments for holding one or more powdered medicaments and one or more solvents. Prior to administration of the medicament(s) the one or more solvents can be admixed with the powder to create the ready-for-use medicament.

Figure 6:
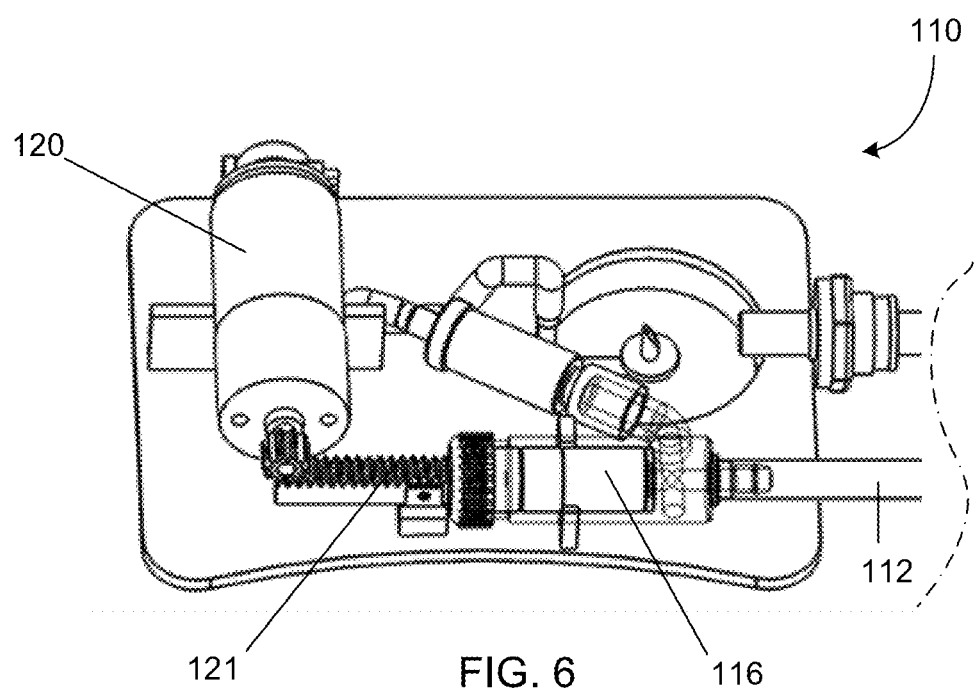
FIG. 6 is an exemplary medicament delivery mechanism located at the base unit of FIGS. 4-5.
Figure 7:
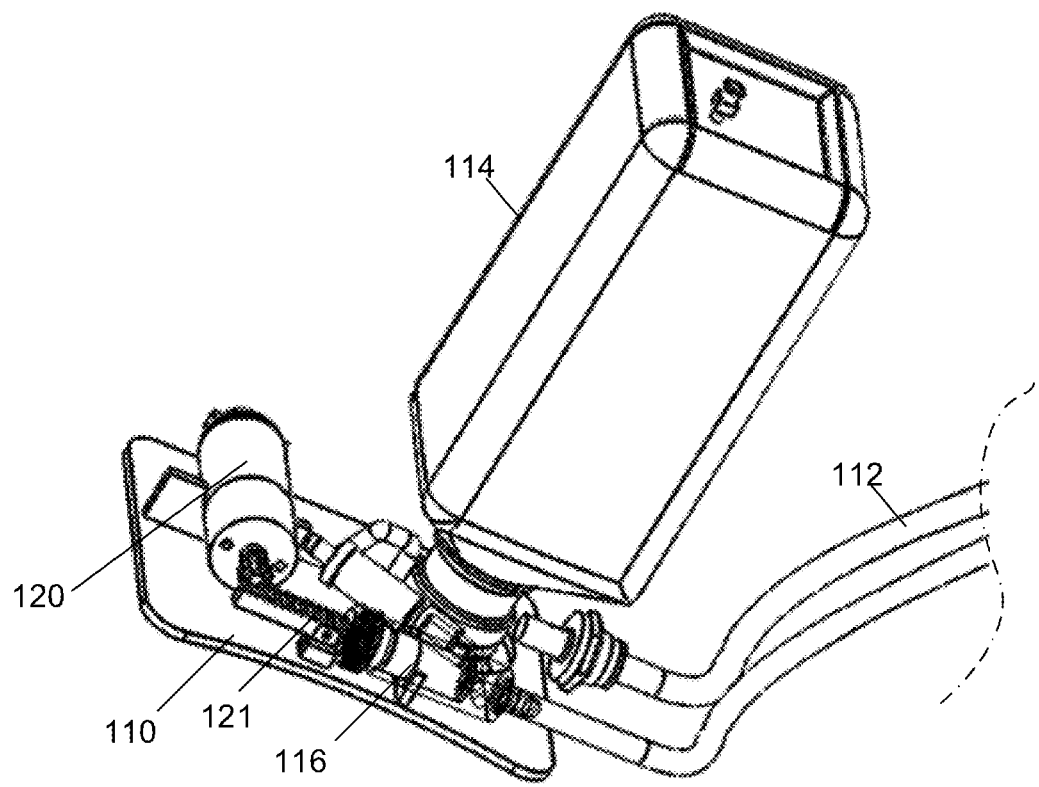
FIG. 7 is the exemplary medicament delivery mechanism of FIG. 6 with a container attached thereto.

Referring to FIGS. 6-7, in certain embodiments, the injection apparatus comprises one or more pumps 116 coupled to base unit 110. In other embodiments, the injection apparatus can comprise one or more pumps 116 located at or within the hand-held unit 102. The pumps 116 can be actuated by one or more motors 120 which can rotate one or more drive shafts 121 coupled to the pumps. The pumps 116 can be piston or plunger pumps, can be connected to the containers 114 (as shown in FIG. 7), and can be configured to pull and/or push a predetermined amount of medicament from each container and deliver the same to the needle 108 in the hand-held unit 102 and into the patient, according to a predefined administration order. The predetermined amounts of each medicament can be equal or different depending on the type of medicament to be administered. The injection apparatus can further comprise one or more motors designed to operate the various components of the apparatus, such as the one or more pumps.

In some embodiments, the injection apparatus can comprise two or more pumps 116 located at the base unit 110, wherein the number of pumps is identical to the number of containers 114, and wherein each pump is coupled to a discrete container 114. In this configuration, each pump 116 is designed to pull and/or push a predetermined amount of medicament from its respective container and to sequentially deliver the medicament to the needle in the hand-held unit 102 and into the patient according to a predefined administration order.

In some embodiments, the injection apparatus can be configured to be suitable for remote locations with limited power supply. In other embodiments, the injection apparatus may be configured to be operated electrically. In some embodiments, the injection apparatus can further comprise a power source located at, for example, the base unit 110, the hand-held unit 102, or both. In some embodiments, the power source can be positioned as a separate power source unit electrically connected to the injection apparatus 102. In some embodiments, the power source is rechargeable. In other embodiments, the power source can be disposable (e.g., disposable batteries). In some embodiments, the injection apparatus further comprises a power-meter configured to display the amount of electricity remaining and/or send an alert when the power reaches a selected level that can interfere with the operation of the injection apparatus.

In use, the injection apparatus is configured to administer the different medicaments sequentially (e.g., one after the other), such that each medicament can be injected at a different injection location. For example, a user can place the hand-held unit 102 at a first injection site on a patient and administer a first medicament, and then the user can move the hand-held unit to a second injection site on the patient and administer a second medicament. This allows a user to inject a single patient with a variety of medicaments that may not be mixable prior to injection. Discrete injection locations for each medicament prevent the medicaments from mixing at the site of injection, thus preventing an adverse reaction at the injection site.

In some embodiments, the injection apparatus can further comprise an injection indicator configured to electrically actuate the valves and/or the one or more pumps 116. For example, in embodiments comprising a single pump, after medicament A is administered, the injection indicator can close a valve positioned at the medicament exit of container A and open a valve positioned at the medicament exit of container B. Thus, when the pump is activated, it can draw medicament only from container B, which has a valve in the open position. Alternatively, in embodiments comprising two or more pumps wherein each pump is associated with a discrete container 114, after injecting medicament A, the injection indicator can turn off pump A associated with container A and activate pump B associated with second container B. Thus, the pumps can be activated according to the order of injections. The injection indicator can furthermore be configured to signal (e.g., visually, auditorily, and/or in a tactile manner such as by vibration) that a medicament has been administered and indicate that the next medicament is ready to be administered.

In certain embodiments, the amount of medicament administered is controlled by an encoder. In some embodiments, the encoder can be coupled to the driving shaft 121 of the pump 116 (e.g., located on the hand-held portion or the base portion). The encoder is configured to, by sensing the amount of rotation of the motor, set the position of the piston head to enable administration of a predetermined amount of medicament. This function is useful when it is desired to set different values for the volumes of the medicament to be injected. The injection volume can be determined for each patient or class of patients, but typically varies from greater than 0 milliliters to about 10 milliliters, and more typically from 0.05 milliliters to 5 milliliters.

In some embodiments, the injection apparatus further comprises a control panel. The control panel can be configured to display desired information related to an injection process to a user and enable him or her to control various functions of the injection process. The control panel can optionally transmit real-time information to a remote device, thus allowing for data storage and/or remote control of the device. In some embodiments, the control panel can control, for example, the amount of each medicament to be administered and/or the injection order of the different medicaments. The control panel can display information such as, for example, the amount of remaining medicament in each container and/or the number of patients that have received medicament, the overall time spent on injection, information regarding the rotation of the motor, etc. As shown in FIG. 2, in some embodiments, the control panel 122 is located at the hand-held unit 102. In other embodiments, the control panel can be located on the base unit 110.

In certain embodiments, the injection apparatus further comprises a volume control apparatus for setting and verifying different volumes of a dose to be injected. In some embodiments, the volume control apparatus can comprise, for example, an encoder, an electrical meter, sensors and indicators for measuring medicament amounts. In other embodiments, the volume control apparatus can comprise a simple fixed piston and plunger that can be adjusted (e.g., manually or electrically) to deliver various amounts.

In some embodiments, each container 114 can comprise a valve actuatable between an open configuration and a closed configuration. In the open configuration, medicament can pass through the valve and in the closed configuration medicament is prevented from passing through the valve. In some embodiments, the valves are non-return or check valves which allow passage of fluid therethrough in only a single direction. In other embodiments, the valves can be configured such that they can be actuated electrically between the open and closed configurations. In still other embodiments, the valves can be configured such that they can be actuated manually (e.g., by pressing a button, flipping a switch, or turning a lever).

Figure 8:
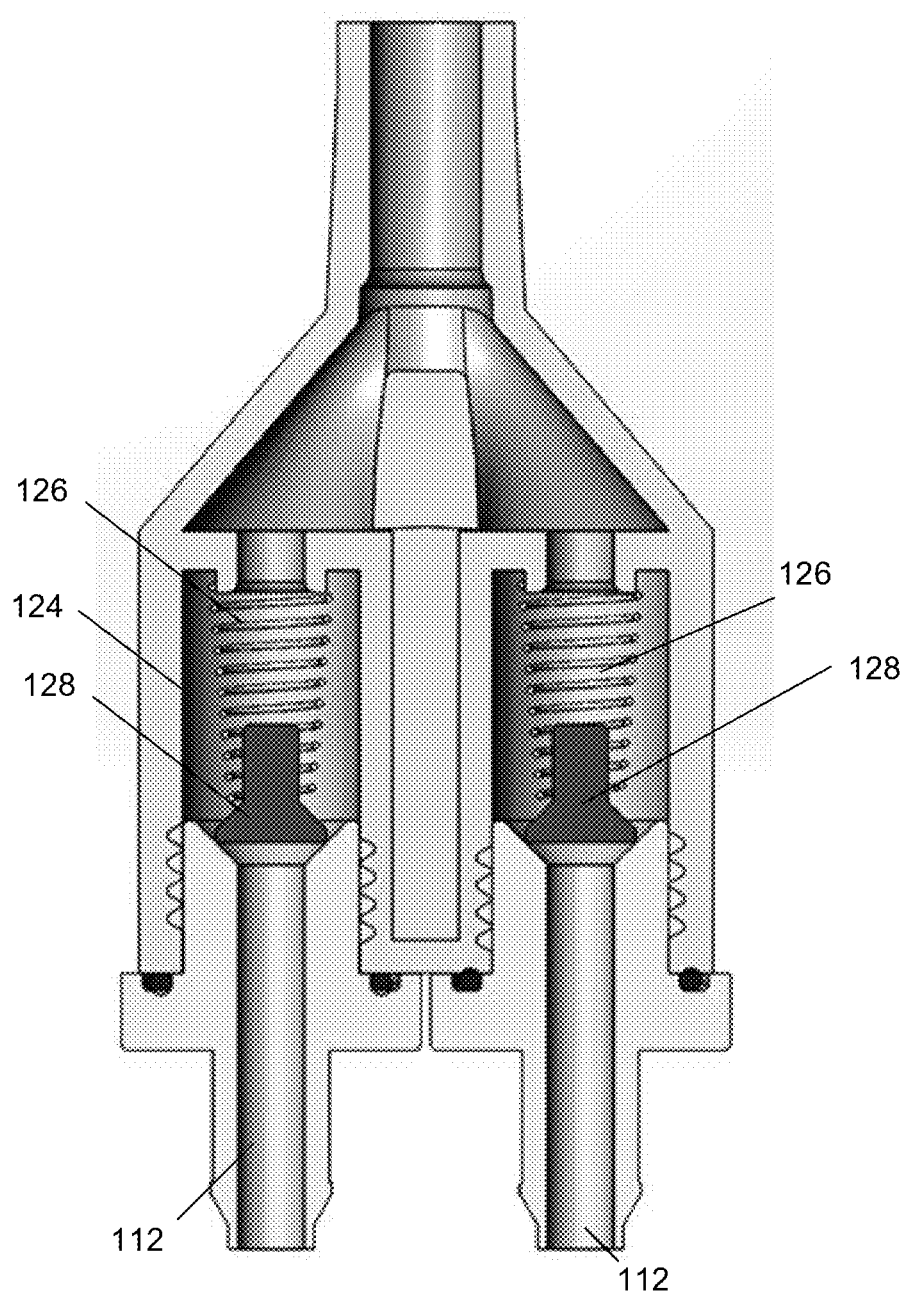
FIG. 8 is an embodiment of a directional valve used in an injection apparatus.
Figure 9:
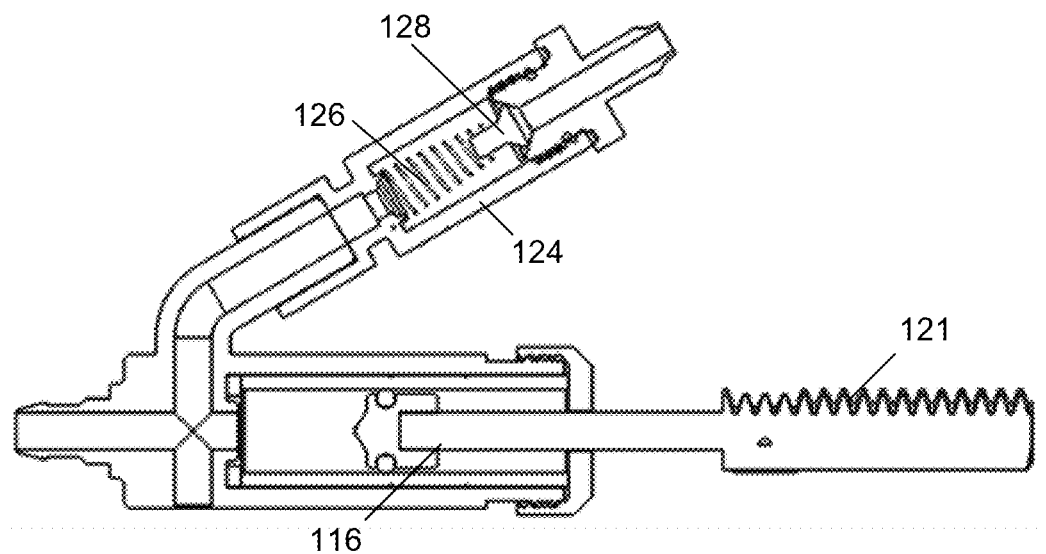
FIG. 9 is a cross sectional view of a medicament delivery mechanism.
Figure 10:
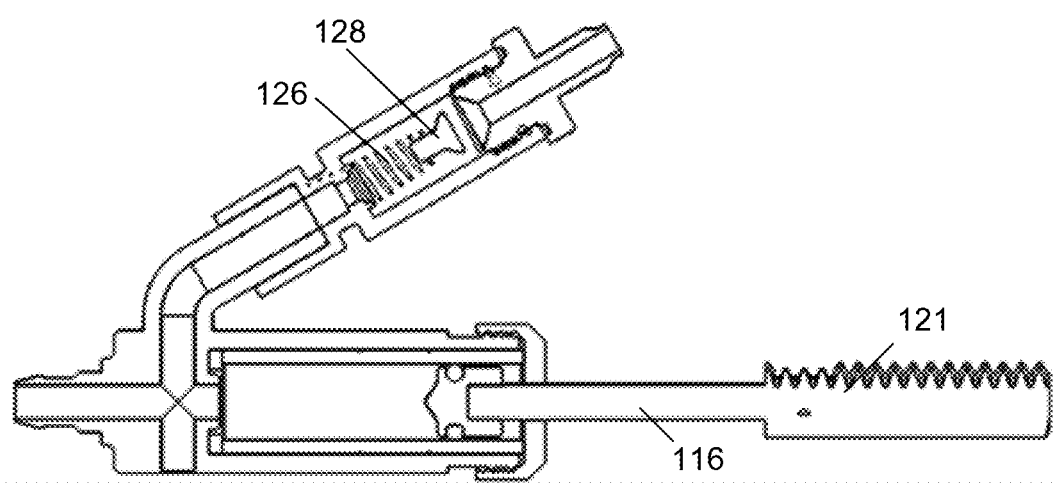
FIG. 10 is a cross sectional view of a medicament delivery mechanism.
Figure 11:
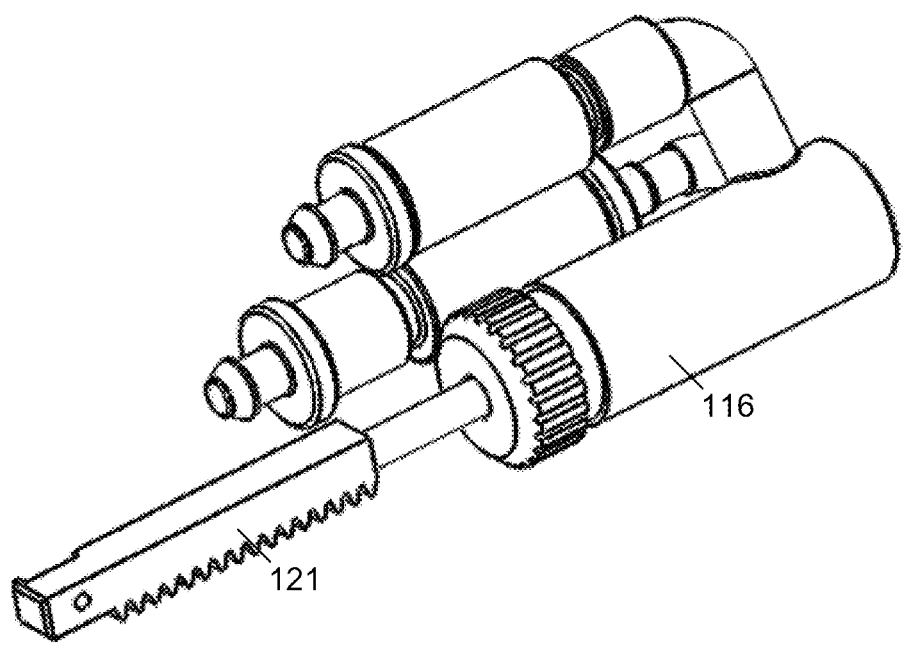
FIG. 11 is a perspective view of a medicament delivery mechanism.
Figure 12:
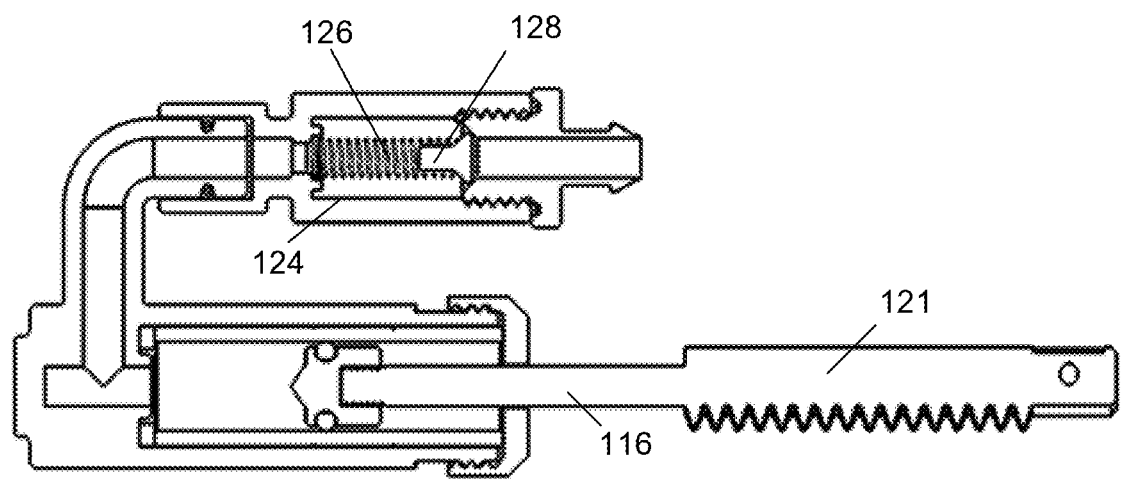
FIG. 12 is a cross sectional view of a medicament delivery mechanism.
Figure 13:
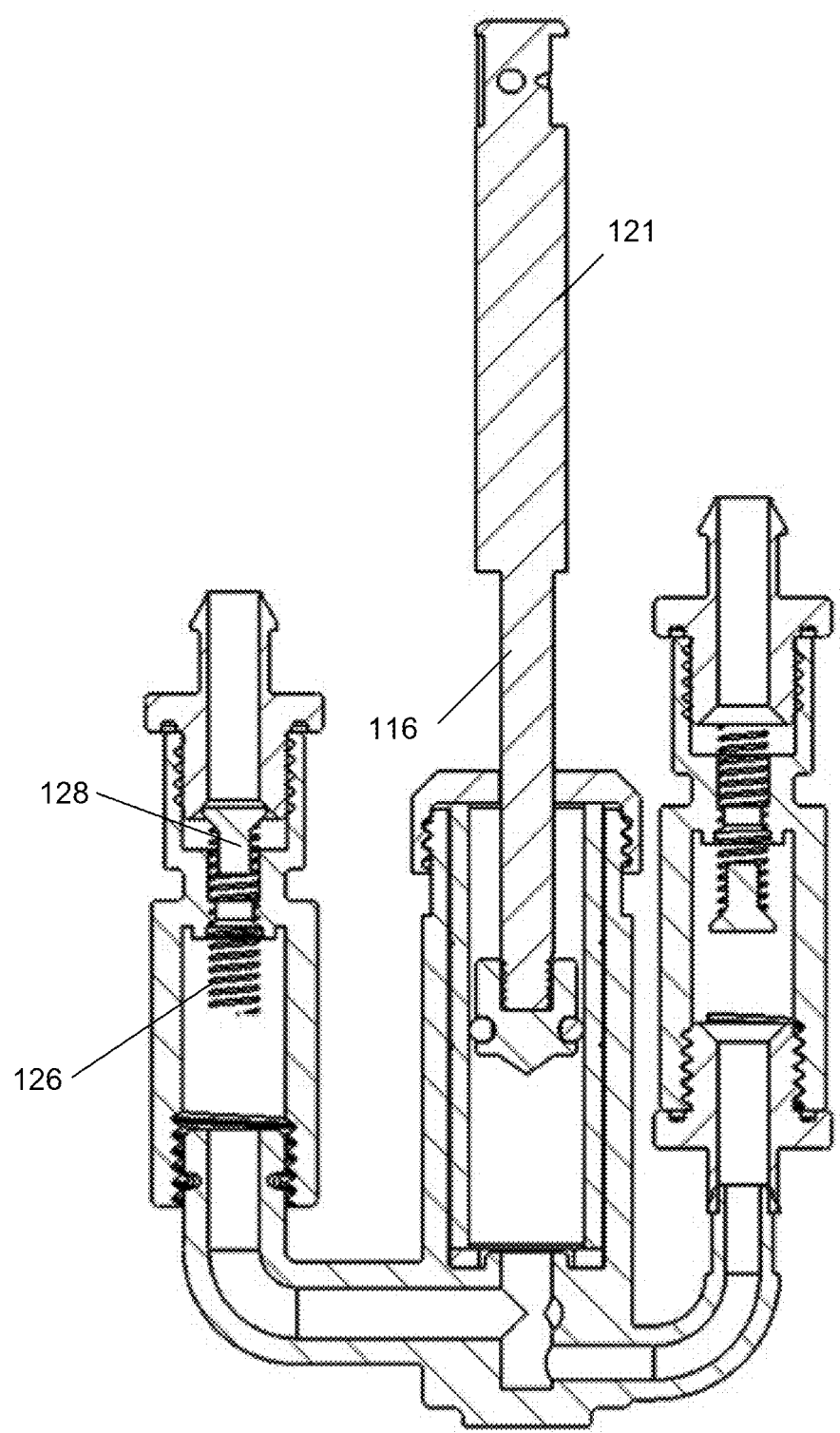
FIG. 13 is a cross sectional view of a medicament delivery mechanism.

Referring now to FIG. 8, in some embodiments, the injection apparatus can further comprise one or more non-return valves 124 (e.g., check valves, inlet non-return valves, lift-check valves, etc.) located, for example, in the hand-held unit. In some embodiments, the injection apparatus comprises a plurality of non-return valves 124 wherein each non-return valve is connected to a different medicament container 114. In some embodiments, the injection apparatus comprises 2, 3, 4, 5, 6, 7, 8, 9, or 10 non-return valves 114, each coupled to the same or different medicament container. Each non-return valve has an open position wherein fluid can flow through the valve and a closed position wherein fluid is prevented from flowing through the valve. The purpose of these non-return valves is to prevent back flow of fluids into the medicament containers, therefore preventing contamination thereof and extending the shelf life of said containers, so that they can be re-used if an amount of medicament remains following the injection procedure.

In embodiments wherein the non-return valve is a check valve, as shown in FIG. 8, the check valve can be configured to allow fluid flow in only one direction (e.g., from the container into the dosing chamber) thus preventing the backflow of medicament into the container, which can result in container contamination and/or an incorrect dosing amount. The particular embodiment of FIG. 8 includes a valve 124 comprising a spring 126 and a stopper 128 (which can be any of various shapes including, for example, a sphere, a disk, a cone, etc.). The spring 126 exerts a biasing force against the stopper 128, biasing the valve into a closed position and preventing fluid from flowing through the valve. If the pressure external to the valve (e.g., in connecting tubes 112) is less that the opening (or "cracking") pressure of the check valve (e.g., less than the force exerted by spring 126), the valve remains closed. This can prevent fluid from the containers from flowing into the dosing chamber until the pump is activated to pressurize the fluid. If the external pressure is greater than the cracking pressure of the check valve, fluid can push the stopper 128 against the spring 126, compressing the spring and allowing fluid flow through the valve in one direction.

FIGS. 9-13 show embodiments of non-return valves 124 coupled to pump 116 in a variety of configurations.

Figure 14:
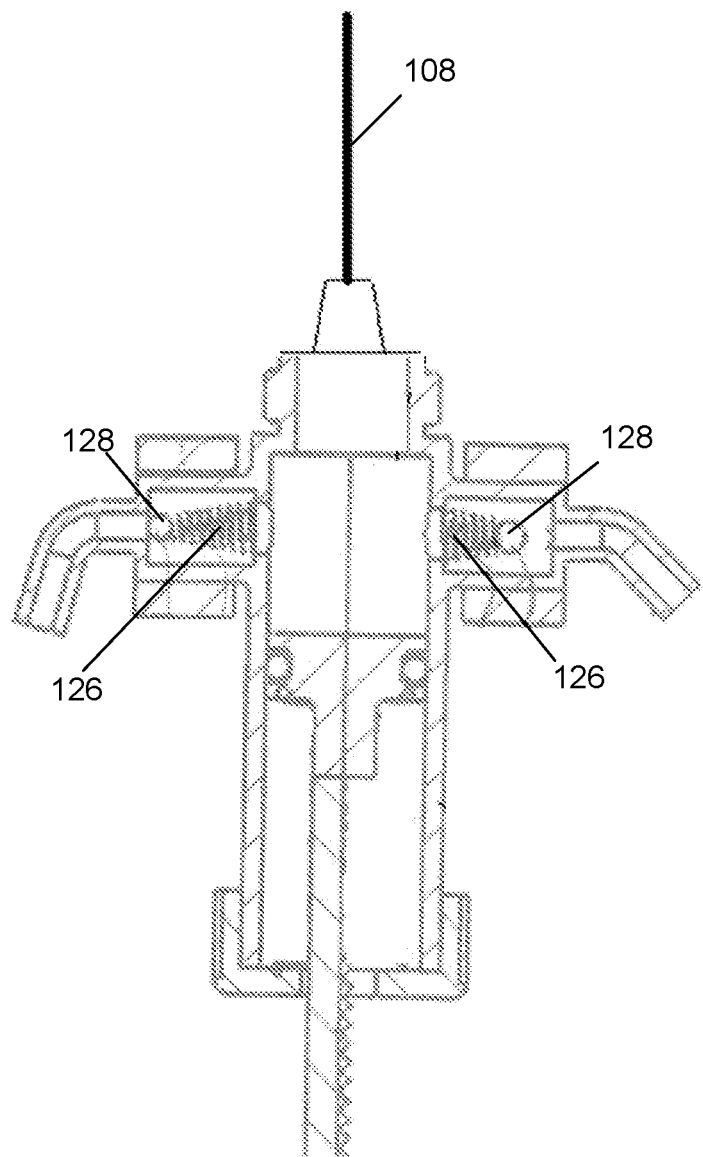
FIG. 14 is an exemplary medicament delivery mechanism comprising a syringe connected to non-return/unidirectional valves.

FIG. 14 shows an embodiment comprising two check valves 124 disposed within the hand-held unit 102 of the injection apparatus 100. The first check valve 124a is shown in the closed position, with stopper 128a in a closed position at the inlet end of the valve. The second check valve 124b is shown in the open position, with stopper 128b spaced apart from the inlet end of the valve and spring 126 in a compressed configuration. This allows fluid to flow through the valve inlet, and out through the needle 108.

In some embodiments, each valve can open and close electronically. In a specific embodiment, said valves are controlled by a microprocessor, which is optionally part of the control unit.

In some embodiments, the injection apparatus can be configured to inject two or more different medicaments into a patient in two or more differing injection locations. In specific embodiments, the injection apparatus can comprise three main subsystems: (1) a hand-held unit comprising a single needle, non-return valves, printed circuit board (PCB), and a screen; (2) a base unit comprising a motor, a pump, non-return valves, PCB, medicament containers, and a power-supply (e.g. batteries); and (3) tubes and electrical wires that connect between the hand-held unit and base-unit.

In some embodiments, an injection apparatus can inject two, three, or four medicaments sequentially into a patient. In such embodiments, for example, the injection apparatus can comprise a hand-held unit 102 comprising an operator grip 104, a head portion 106, and a single stationary needle 108. The injection apparatus can further comprise a base unit 110 coupled to the hand-held unit 102 via two, three or four connecting tubes 112, corresponding to two, three, or four containers 114, respectively. The two, three or four containers 114 can each hold a different medicament, and each container can be removably coupled to the base unit 110. The injection apparatus can further comprise a power source, an injection indicator for identifying that a medicament has been administered and determining and/or indicating which medicament is to be administered next, and a control panel for determining and/or displaying various functions of the injection process. In some embodiments, the injection indicator and the control panel can be automated components coupled to the power source.

Figure 15:
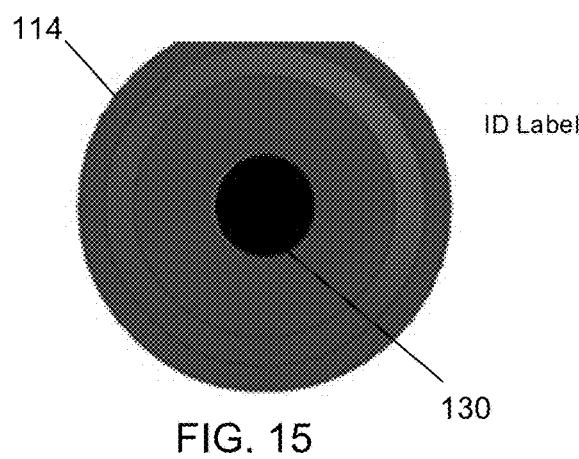
FIG. 15 is an exemplary identification mechanism of a container holding a medicament.
Figure 16:
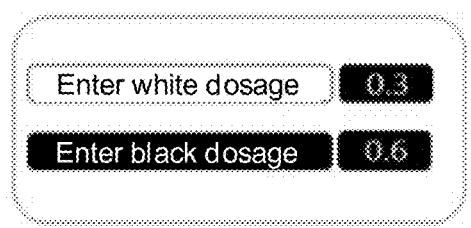
FIG. 16 is an exemplary format for an identification mechanism.
Figure 17:
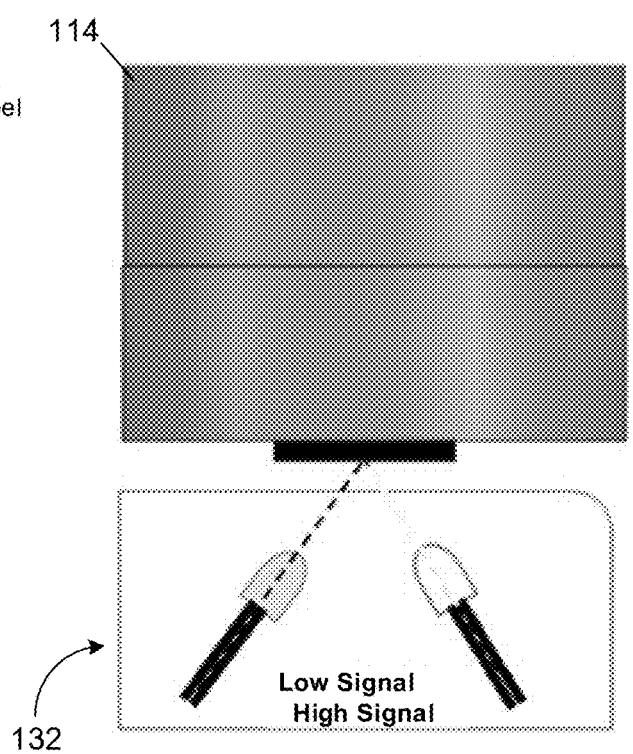
FIG. 17 is an exemplary reader unit for use with a container.

Referring now to FIGS. 15-17, in certain embodiments, each container 114 of the injection apparatus further comprises an identification marker 130. The identification marker 130 can be any suitable marker for conveying information (e.g., an RFID code, a QR-code, a barcode, a color sticker, etc). In some embodiments, the identification marker 130 indicates, for example, the type of medicament within each container, the amount of medicament that needs to be administered from each container, the manufacturing date, and/or the expiration date. Accordingly, in some embodiments, the injection apparatus further comprises a reader unit 132 configured to read the identification markers 130 and to transmit the data to the control unit and/or to a remote unit.

In some embodiments, the reader unit 132 can be configured to emit and receive light. In such embodiments, the identification markers 130 can be comprised of light absorbing materials and/or a light reflecting materials. For example, a first container can have a light-absorbing sticker (e.g., a black sticker) and a second container can comprise a light-reflecting sticker (e.g., a white sticker). When a container is coupled to the base unit, the reader unit can read the identification marker in order to distinguish between the first and second containers and determine the contents and/or required dosage for each container. The reader unit can then transmit that information to the control unit and/or a remote unit.

In some embodiments, the injection apparatus is essentially formed of two parts, a medicament storage and temperature control unit housed in a backpack, and a hand-held unit coupled to and fed from the backpack. In such embodiments, the medicament can be pumped through the temperature control unit to bring it to an optimal administration temperature. The medicament can then be administered in precise dosages via an injection pumpdisposed within the hand-held unit In some embodiments, the injection apparatus can be configured to administer, for example, 3 liters (approximately 2.55 kg) of vaccine in a 6-hour time frame. In some embodiments, the container(s) can be sized such that the operator can carry 1 to 2 L of medicament within the container(s) of the base unit in the backpack and can refill the containers from a central location when required. This prevents the injection apparatus from becoming too heavy for easy transportation by a user. In some embodiments, for example, the weight of the injection apparatus should not exceed 5 kg.

Figure 18:
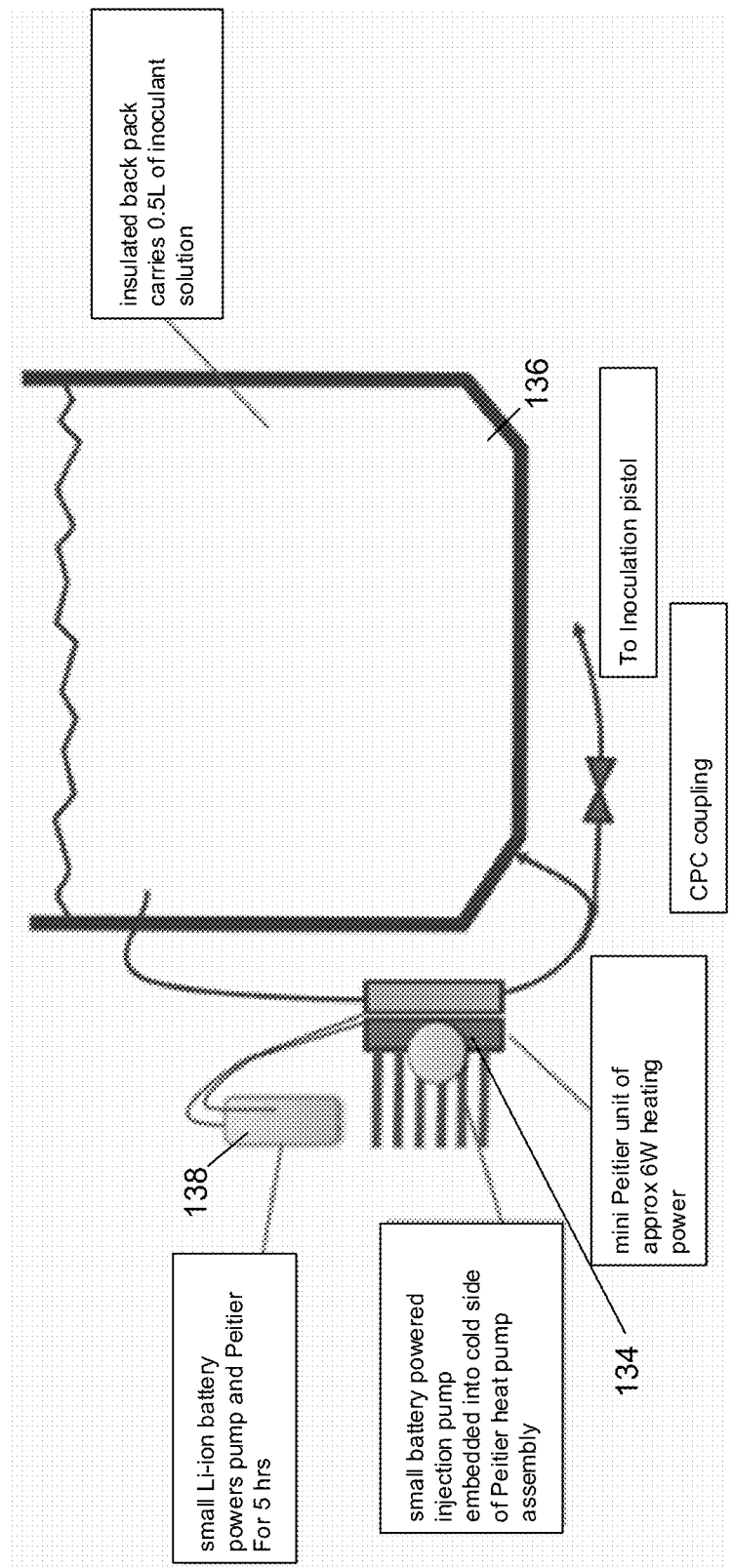
FIG. 18 is an exemplary Peltier heating or cooling pump system.

Referring to FIG. 18, in some embodiments, the injection apparatus further comprises one or more temperature control units 134 for heating and/or cooling the medicament to be administered. This is especially advantageous for medicaments that must be pre-heated (e.g., to a temperature at or near the patient's body temperature), prior to administration. In the illustrated embodiment, the temperature control unit 134 is coupled to the backpack portion 136 of the injection apparatus. In other embodiments, a separate temperature control unit 134 may be coupled to each container 114 holding a medicament that needs to be heated and/or cooled. Alternatively, a temperature control unit can be positioned along the connecting tube 112 and/or at a location near to the needle 108 to heat and/or cool the medicament prior to its administration.

In a specific embodiment, the temperature control unit can use heat generated by the motor of the injection apparatus to help heat the medicament. The temperature control unit can be configured such that it has the capacity to heat and/or cool 3 kg of medicament. The temperature control unit can be configured such that the temperature of the medicament at the time of injection has a variance of no more than +/−1° C. from the desired temperature.

The temperature control unit used can be selected according to the system requirements. In some embodiments, the heat used to raise the temperature can be generated by the engine or motor of the injection apparatus, and/or by a Peltier device. This can reduce energy consumption, as well as improving cost and performance of the apparatus.

For example, as shown in FIG. 18, a small Li-Ion battery 138 can be used to power a Peltier device 134 which supplies heat to or removes heat from the medicament until a desired temperature is reached. Notably, the system controls the temperature to prevent overheating of the medicament, which could, in some cases, render it unusable. In this way, the battery energy of the apparatus can be used more efficiently since the batteries only need to supply a portion of the heating energy. Peltier devices work best when the "temperature lift" (e.g., the difference in temperature between the hot side and cold side) is kept to a minimum. For example, in some embodiments, the lift can be approximately 10° C. which is low enough to enable the Peltier to operate efficiently. In an exemplary embodiment, a Coefficient of Performance (COPh) of approximately 3 can be achieved thereby reducing the battery requirement to ⅓ of the battery energy required by a "battery only" system. In practical terms, this energy load could be realized by, for example, a Li-ion battery of around 50 g with dimensions of 50×50×10 mm, capacity 2500 mAH, and power 1.8-2 W.

In some embodiments, the Peltier device can be used in conjunction with waste heat from the motor of the injection device by capturing the waste heat and using it as additional heat input to the "cold side" of the Peltier device. In an exemplary motor, the efficiency can be around 60%, and therefore 1-2 W of heat can be generated in the motor body. This additional heat can be utilized by the Peltier device, and thus improve the overall heat pump performance as well as substantially reduce the battery energy budget.

Accordingly, in certain embodiments, the injection apparatus of the invention comprises a heat generating unit which is based on a Peltier/pump motor assisted heating. The amount of medicament injected by the Peltier/pump motor assisted heating apparatus is critical. As such, the injection apparatus may require calibration prior to an initial use, or prior to each use. Accordingly, in certain embodiments, the injection apparatus further comprises an encoder for calibrating the location of the piston or the pump, to thereby obtain accurate calibration.

Many known injection devices use manual calibration of the injection dosage, which can result in large deviations within the amount of injected medicament due to, for example, operator error and the inaccuracy of cylinder measuring techniques. In contrast, in some embodiments, the instant encoder can enable radial resolution of 5 degrees, which leads to a linear movement of as little as 0.0006 mm of the piston, and therefore provides high dosage precision. However, over time dosage deviations can occur due to manufacturing tolerances resulting in cylinder differences and/or certain degrees of freedom between moving mechanical parts that change due to corrosion and abrasion. Accordingly, in certain embodiments, each injection apparatus can be calibrated during manufacturing and additionally calibrated by the end user according to need, prior to each use, or periodically.

Figure 19:
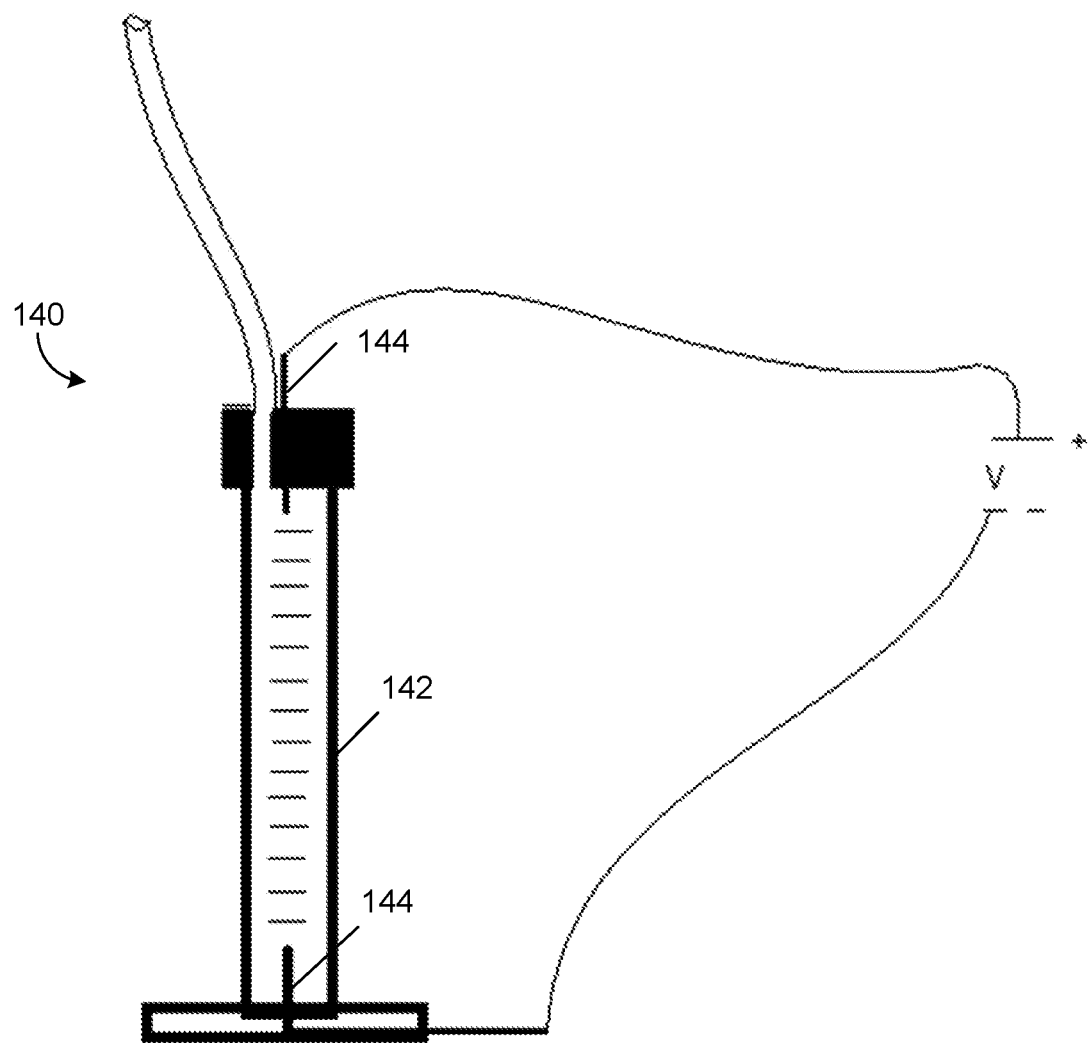
FIG. 19 is an exemplary calibration system of the injection apparatus.

Accordingly, in some embodiments, the injection apparatus further comprises an automated calibration system that enables an end user to calibrate the injection apparatus. As shown in FIG. 19, in such embodiments, the automated calibration system 140 may comprise a sealed container 140 with electrodes 142 at its bottom and top, wherein the dimensions of the container and therefore the distance between the electrodes is known. To calibrate the apparatus, the user can turn the injection apparatus to a "calibration mode" such that the apparatus will inject a predetermined amount of liquid (e.g. 1 cc of water) into the sealed container. Once the liquid reaches the top electrode, the calibration system notifies the apparatus and stops the injections. The calibration system determines the amount of injections that were required to fill the known volume of the container, calculates the volume of each injection, and compares it to the predetermined amount of each injection. This allows the calibration system to determine if there is any discrepancy in the amount and enables the calibration system to automatically calibrate the injection apparatus in accordance with the measured discrepancy.

In certain embodiments, the injection apparatus further comprises a control unit capable of identifying malfunctions in the injection procedure, such as partial injection(s), clogging, air bubbles within the tubes, leakage, and/or emptying of the containers. The control unit can additionally identify malfunctions within the different components of the injection apparatus, such as low power, faulty pump(s), torn tube(s), etc.

Incomplete injection and other malfunctions can occur due to human error, (e.g., when a user withdraws the needle out of the patient's body before all the medicament has been administered), or due to mechanical malfunction (e.g., the piston not moving all the way forward within the dosing chamber to expel the medicament, clogging of the tubes or of the needle, for example, due to dirt or viscosity of the liquid, and air bubbles infiltrating the system which may alter the final volume of the injected medicament). Regardless of cause, incomplete rejection results in the patient receiving only a portion of the intended dosage of medicament. These malfunctions may prevent the accurate administration of a medicament to the patient or prolong the duration of each injection.

In certain embodiments, the injection apparatus further comprises a malfunction-identification system, which can be configured to identify the above described malfunctions, as well as others, and send an alert to the user. Such a malfunction-identification system can comprise various mechanisms, for example, a probe at the needle or needle head that identifies an early withdrawal of the apparatus prior to the completion of the injection, a probe coupled to the dosing chamber that identifies whether the piston head moves all the way to the end of the dosing chamber, a probe at the piston head that identifies whether the head of the piston moves backwardly before the piston head moves all the way to the end of the dosing chamber (e.g., indicative of an incomplete injection), a sensor that identifies whether the piston does not move or moves very slowly (e.g. using the encoder and internal clock) which can be indicative of a clog, and/or a sensor that identifies whether the plunger moves too fast (e.g. using the encoder and internal clock) which can be indicative of an air bubble or leakage. The malfunction-identification system can further function to calculate the remaining amount of medicament in each container (e.g., by multiplying the number of injections by the injection dosage), measure the current used to activate the motor, which can correspond to the presence of an air bubble, leakage or a clog, etc. The malfunction-identification system can further be configured to measure the duration of each injection and/or the electric current used, wherein any additional duration and/or current used beyond a certain amount can indicate clogging within the system, and any decrease in duration and/or current used beyond a certain amount can indicate an air bubble or leak within the system, or the end of the medicament in the container.

In certain embodiments, two or more hand-held units can be connected to the same base unit, thereby allowing two or more operators to work side by side to administer medicament from the same containers. This reduces costs as there is need for only one base unit and processing system to control the injection amounts and/or order.

III. Examples

Example 1

The following example provides a representative method for heating the medicament using an injection apparatus according to the embodiments described herein.

The medicament. In the instant example, the medicament is a vaccine for inoculating poultry which is administered at a temperature of approximately 38° C. The vaccine is a protein in a mineral oil emulsion with a specific heat capacity of 2130 J/kg.

Heating energy. The vaccine is to be heated from approximately 28° C. (chicken house temperature) to 38° C. The liquid temperature at the time of injection should be within an accuracy of +/−1° C. The total heat requirement is therefore 54315 J or 0.15 kwh (Q=2.55*2130*10). In addition, there is the pumping energy and pump motor cooling to be considered. This can add an extra 40-50,000 J to the energy requirement.

Assuming a 6 hour working day, the heating power required is 2.5 W (P=54315/(6*3600). The injection pump is also expected to add another about 3 W to the energy load, and hence the overall power demand is about 5-6 W. The heating system should prevent overheating of the inoculant.

In view of the many possible embodiments to which the principles of the disclosure may be applied, it should be recognized that the illustrated embodiments are only preferred examples and should not be taken as limiting the scope of the disclosure. Rather the scope of the disclosure is defined by the following claims.

The invention claimed is:

1. An injection apparatus, comprising:
a single needle;
a plurality of dosing chambers fluidly coupled to the single needle;
a needle sensor configured to determine an insertion depth of the single needle into a patient;
at least one pump fluidly coupled to the plurality of dosing chambers, the at least one pump including a linear toothed driving shaft;
at least one motor including a toothed gear configured to actuate the linear toothed driving shaft of the at least one pump;
wherein the injection apparatus is configured to administer a plurality of medicaments sequentially at a plurality of injection sites; and
wherein the injection apparatus is configured to administer a medicament of the plurality of medicaments automatically upon insertion of the single needle to a selected depth within the patient.

2. The injection apparatus of claim 1, further comprising a plurality of medicament containers, each medicament container being fluidly coupled to a dosing chamber of the plurality of dosing chambers.

3. The injection apparatus of claim 2, further comprising one or more flexible connecting tubes fluidly coupling the plurality of dosing chambers and the plurality of medicament containers and configured to resist widening upon the passage of medicament therethrough.

4. A method, comprising: providing the injection apparatus according to claim 1; and using the injection apparatus.

5. The method of claim 4, wherein the method comprises:
pressing a head portion of the injection apparatus against a body of a patient at a first injection location, the injection apparatus comprising a hand-held unit fluidly coupled to a base unit, the hand-held unit comprising the single needle and the plurality of dosing chambers, the base unit comprising a plurality of medicament containers;
administering a first medicament of the plurality of medicaments to the patient;

pressing the head portion of the injection apparatus against the body of the patient at a second injection location; and administering a second medicament of the plurality of medicaments to the patient.

6. The method of claim 5, further comprising:

pressing the head portion of the injection apparatus against the body of the patient at a third injection location; and administering a third medicament of the plurality of medicaments to the patient.

7. An injection apparatus, comprising:

a hand-held unit comprising a head portion having a first end, a second end, and an intermediate segment between the first and second ends, a gripping portion extending at an angle from the intermediate segment of the head portion, and a single needle positioned at the first end of the head portion;

a control panel configured to determine and display information relating to an injection process, the control panel coupled to the second end of the head portion of the hand-held unit;

a plurality of dosing chambers fluidly coupled to the single needle;

a base unit coupled to a plurality of medicament containers;

at least one flexible connecting tube fluidly coupling the hand-held unit and the base unit, the flexible connecting tube configured to resist widening upon passage of medicament therethrough;

at least one pump configured to pump medicament from the base unit to the hand-held unit, the at least one pump including a linear toothed member;

at least one motor including a toothed gear configured to actuate the linear toothed member of the at least one pump; and a needle sensor configured to determine an insertion depth of the single needle into a patient, wherein the medicament is administered automatically upon insertion of the single needle to a selected depth into the patient.

8. The injection apparatus of claim 7, wherein the head portion is a stationary head portion and the single needle extends from the head portion.

9. The injection apparatus of claim 7, wherein the head portion is movable relative to the single needle, and wherein urging the head portion rearwardly with respect to the body of a patient exposes the needle.

10. The injection apparatus of claim 7, wherein the base unit is configured to be worn by a user.

11. The injection apparatus of claim 7, further comprising a temperature control unit coupled to the base unit.

12. The injection apparatus of claim 11, wherein the temperature control unit is a Peltier heating and cooling system.

13. The injection apparatus of claim 7, wherein the control panel is configured to transmit data in real-time to a remote device.

14. The injection apparatus of claim 7, further comprising a plurality of valves each being coupled to a medicament container of the plurality of medicament containers.

15. The injection apparatus of claim 7, wherein the injection apparatus is configured to administer a plurality of medicaments sequentially at a plurality of injection sites.

16. The injection apparatus of claim 7, further comprising a malfunction-identification system.

17. The injection apparatus of claim 7, wherein the at least one pump is a plurality of pumps each coupled to one of the plurality of medicament containers.

18. An injection apparatus, comprising:

a hand-held unit comprising a gripping portion, a head portion, and a single needle;

a plurality of dosing chambers fluidly coupled to the single needle;

a base unit coupled to a plurality of medicament containers;

at least one flexible connecting tube fluidly coupling the hand-held unit and the base unit, the flexible connecting tube configured to resist widening upon passage of medicament therethrough;

at least one pump configured to pump medicament from the base unit to the hand-held unit, the at least one pump including a linear toothed driving shaft;

at least one motor including a toothed gear configured to actuate the linear toothed driving shaft of the at least one pump;

a needle sensor configured to determine an insertion depth of the single needle into a patient, wherein the medicament is administered automatically upon insertion of the single needle to a selected depth into the patient;

one or more temperature control units operatively coupled to the medicament containers, wherein the one or more temperature control units are one or more Peltier heating and cooling systems;

one or more control panels configured to determine and display information relating to an injection process and to optionally transmit real-time data to a remote device; and a malfunction-identification system configured to identify malfunction of the injection apparatus.

* * * * *